US009693958B2

(12) United States Patent
Zhu

(10) Patent No.: US 9,693,958 B2
(45) Date of Patent: Jul. 4, 2017

(54) METHODS AND DEVICES FOR PREPARATION OF LIPID NANOPARTICLES

(71) Applicant: Cureport, Inc., Worcester, MA (US)

(72) Inventor: De-Min Zhu, Westborough, MA (US)

(73) Assignee: Cureport, Inc., Worcester, MA (US)

( * ) Notice: Subject to any disclaimer, the term of this patent is extended or adjusted under 35 U.S.C. 154(b) by 84 days.

(21) Appl. No.: 14/209,187

(22) Filed: Mar. 13, 2014

(65) Prior Publication Data

US 2014/0348900 A1 Nov. 27, 2014

Related U.S. Application Data

(60) Provisional application No. 61/791,054, filed on Mar. 15, 2013.

(51) Int. Cl.
*A61K 9/127* (2006.01)
*A61K 31/704* (2006.01)
(Continued)

(52) U.S. Cl.
CPC .......... *A61K 9/1277* (2013.01); *A61K 9/5192* (2013.01); *A61K 31/704* (2013.01);
(Continued)

(58) Field of Classification Search
None
See application file for complete search history.

(56) References Cited

U.S. PATENT DOCUMENTS 4,895,452 A * 1/1990 Yiournas ............... B01F 5/0057
264/4.1
5,030,453 A 7/1991 Lenk et al.
(Continued)

FOREIGN PATENT DOCUMENTS

CA WO 0105373 A1 * 1/2001 ........... A61K 9/1272
WO 01/05373 A1 1/2001
(Continued)

OTHER PUBLICATIONS

B Yu, RJ Lee, LJ Lee. "Macrofluidic Methods for Production of Liposomes." Methods in Enzymology, vol. 465, 2009, ISSN 0076-6879, Chapter 7, pp. 129-141.*
(Continued)

*Primary Examiner* — Isaac Shomer
(74) *Attorney, Agent, or Firm* — Nutter McClennen & Fish LLP; Konstantin Linnik

(57) ABSTRACT

The present invention provides for a process for preparing liposomes, lipid discs, and other lipid nanoparticles using a multi-port manifold, wherein the lipid solution stream, containing an organic solvent, is mixed with two or more streams of aqueous solution (e.g., buffer). In some aspects, at least some of the streams of the lipid and aqueous solutions are not directly opposite of each other. Thus, the process does not require dilution of the organic solvent as an additional step. In some embodiments, one of the solutions may also contain an active pharmaceutical ingredient (API). This invention provides a robust process of liposome manufacturing with different lipid formulations and different payloads. Particle size, morphology, and the manufacturing scale can be controlled by altering the port size and number of the manifold ports, and by selecting the flow rate or flow velocity of the lipid and aqueous solutions.

25 Claims, 9 Drawing Sheets

(51) Int. Cl.
*C12N 15/113* (2010.01)
*A61K 9/51* (2006.01)

(52) U.S. Cl.
CPC ......... *C12N 15/113* (2013.01); *Y10S 977/773* (2013.01); *Y10S 977/907* (2013.01)

(56) References Cited

U.S. PATENT DOCUMENTS

| | | | |
|---|---|---|---|
| 5,032,457 A * | 7/1991 | Wallach | A61K 9/127 264/4.1 |
| 5,145,256 A * | 9/1992 | Wiemers | B01F 5/061 137/808 |
| 5,192,549 A | 3/1993 | Barenolz et al. | |
| 5,316,771 A | 5/1994 | Barenholz et al. | |
| 5,380,531 A | 1/1995 | Chakrabarti et al. | |
| 5,785,987 A | 7/1998 | Hope et al. | |
| 5,891,467 A | 4/1999 | Willis | |
| 5,962,016 A | 10/1999 | Willis | |
| 6,680,068 B2 | 1/2004 | Campbell et al. | |
| 7,901,708 B2 | 3/2011 | MacLachlan et al. | |
| 8,067,390 B2 | 11/2011 | Merritt et al. | |
| 2004/0142025 A1* | 7/2004 | MacLachlan | A61K 9/127 424/450 |
| 2004/0208921 A1 | 10/2004 | Ho et al. | |
| 2007/0042021 A1 | 2/2007 | Schiffrin et al. | |
| 2008/0171077 A1* | 7/2008 | Gray | A61K 31/7105 424/450 |
| 2008/0171078 A1* | 7/2008 | Gray | A61K 9/127 424/450 |
| 2010/0233275 A1 | 9/2010 | Saulnier et al. | |
| 2011/0038941 A1 | 2/2011 | Lee et al. | |

FOREIGN PATENT DOCUMENTS

| | | |
|---|---|---|
| WO | 02/100435 A1 | 12/2002 |
| WO | 03/015757 A1 | 2/2003 |
| WO | 2004/029213 A2 | 4/2004 |
| WO | 2006/102395 A2 | 9/2006 |
| WO | 2009/120247 A2 | 10/2009 |

OTHER PUBLICATIONS

A Jahn, JE Reiner, WN Vreeland, DL DeVoe, LE Locascio, M Gaitan. "Preparation of nanoparticles by continuous-flow microfluidics." Journal of Nanoparticle Research, vol. 10, 2008, pp. 925-934.*

J Yuan, SM Hira, GF Strouse, LS Hirst. "Lipid Bilayer Discs and Banded Tubules: Photoinduced Lipid Sorting in Ternary Mixtures." Journal of the American Chemical Society, vol. 130, 2008, pp. 2067-2072.*

Flowmeters.com. Laboratory Flow Meters: Flow Measurement in the Lab. http://www.flowmeters.co.uk/flowmetersnewsblog/laboratoryflowmetersflowmeasurementinthelab/, accessed by examiner on Sep. 26, 2016, 4 printed pages.* efunda Reynolds Number Calculator. http://www.efunda.com/formulae/fluids/calc_reynolds.cfm#calc, accessed by examiner Sep. 26, 2016, 1 printed page.*

International Search Report and Written Opinion for Application No. PCT/US2014/027064, mailed Jul. 21, 2014 (13 pages).

Yu et al., Microfluidic assembly of lipid-based oligonucleotide nanoparticles. Anticancer Res. Mar. 2011;31(3):771-6.

Belliveau, N. M., et al., "Microfluidic Synthesis of Highly Potent Limit-size Lipid Nanoparticles for In Vivo Delivery of siRNA", Nucl. Acids Molec. Biol., 2012; v. 1, pp. 1-9.

Extended European Search Report for European Application No. 14769279.2, issued May 3, 2016 (10 pages).

Jahn, A., et al., "Controlled Vesicle Self-Assembly in Microfluidic Channels with Hydrodynamic Focusing," JACS Communications, 2004, v. 126, pp. 2674-2675.

Jahn, A., et al., "Microfluidic Directed Formation of Liposomes of Controlled Size," Langmuir, 2007, v. 23, pp. 6289-6293.

Rudra, A., et al., "Doxorubicin-loaded phosphatidylethanolamine-conjugated nanoliposomes: in vitro characterization and their accumulation in liver, kidneys, and lungs in rats," Intl J Nanomedicine; 2010, v. 5, pp. 811-823.

Zhigaltsev, I. V. et al., "Bottom-up design and synthesis of limit size lipid nanoparticle systems with aqueous and triglyceride cores using millisecond microfluidic mixing," Langmuir (ACS Publications), 2012, v. 28, pp. 3633-3640.

* cited by examiner

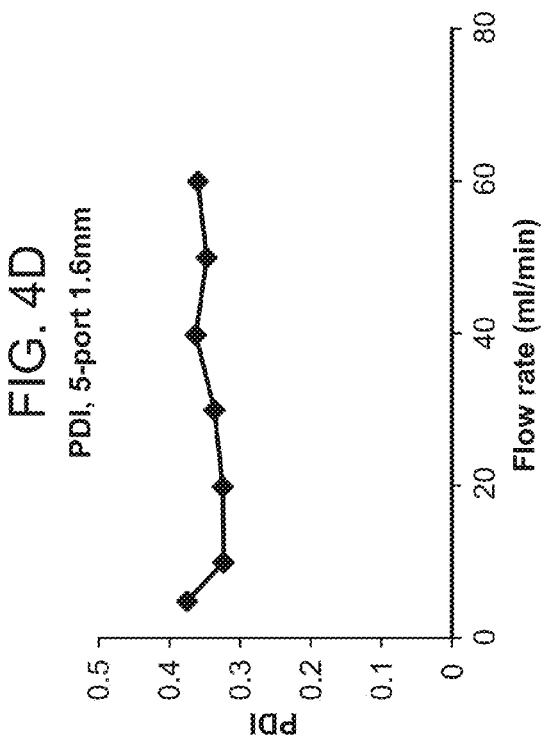
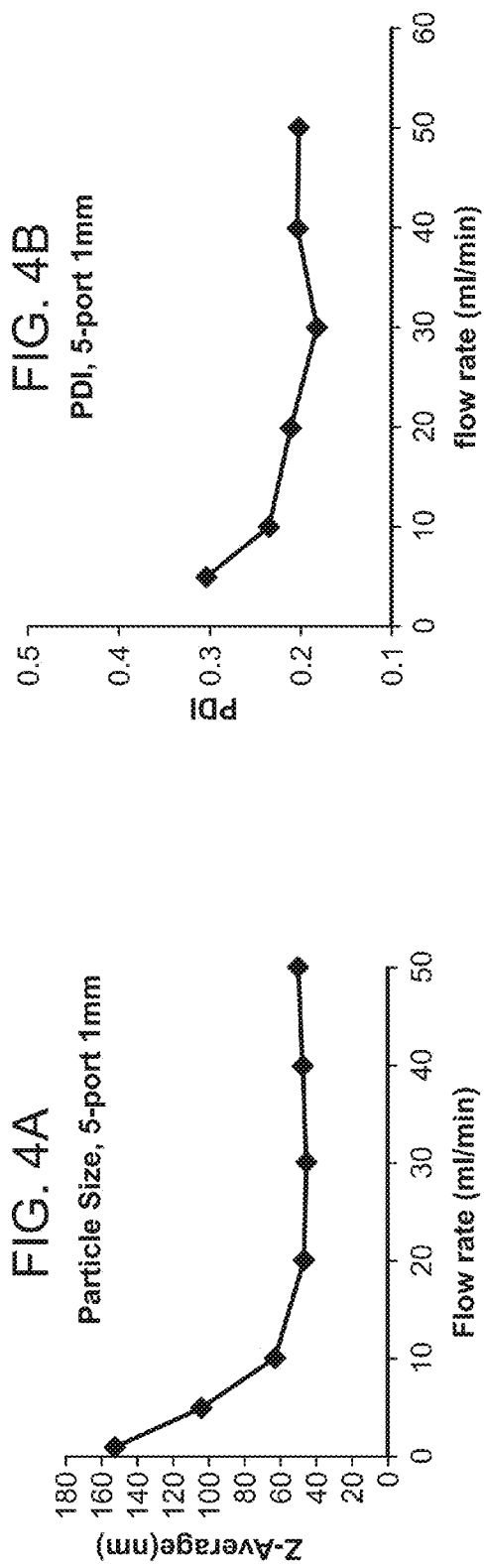
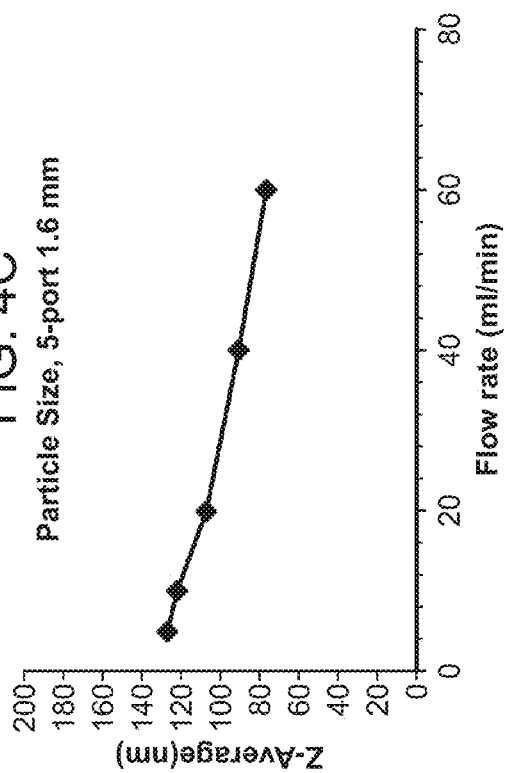

Particle Size, 5-port 1mm

PDI, 5-port 1mm

Particle Size, 5-port 1.6mm

PDI, 5-port 1.6mm

METHODS AND DEVICES FOR PREPARATION OF LIPID NANOPARTICLES

This application claims priority to U.S. provisional patent application No. 61/791,054, filed on Mar. 15, 2013, which is hereby incorporated by reference in its entirety.

FIELD OF THE INVENTION

The present technology generally relates to liposomes and, more specifically, to liposomes encapsulating an active pharmaceutical ingredient.

BACKGROUND

Liposome technology has been utilized for drug delivery in clinical therapy and scientific research. The current methods for liposome preparation are used largely for small-scale laboratory research. Exemplary methods include a lipid dry film rehydration/extrusion method, a detergent dialysis method, and an ethanol evaporation and dilution method.

U.S. Pat. No. 7,901,708 and US Patent Publication No. 2007/0042021, incorporated herein by reference, refer to a two-step method for liposome preparation: (i) using a T-connector to mix a lipid-organic solvent solution with an aqueous solution; (ii) diluting the mixture with an aqueous solution.

The currently available methods present difficult problems associated with scalability, low reproducibility and product heterogeneity. There exists a need for improved methods to make liposomes for use in drug delivery.

SUMMARY OF THE INVENTION

The present invention provides a method for preparing lipid nanoparticles (LNP). In preferred aspects, the method comprises:

a) introducing i) one or more streams of a lipid solution via a first set of one or more inlet ports of a manifold and ii) one or more streams of an aqueous solution via a second set of one or more an inlet ports of the manifold, thereby mixing the lipid solution and the aqueous solution so as to produce an LNP solution; and b) recovering the LNP solution via one or more outlet ports of the manifold. In the above method, the angle between at least one lipid and at one aqueous solution inlet ports is not 180° or a substantially similar angle. In other words, at least one stream of lipid solution and at one stream of aqueous solution collide at an angle less than about 180°. Thus, in some aspects, the method does not include a T-connector.

The invention also provides the LNP solution made by the above method, a pharmaceutical composition prepared using the LNP solution.

The invention further provides a device adapted to perform the method, such as a manifold system described in detail below.

The present invention also provides a method for producing LNP containing an active pharmaceutical ingredient ("API"), wherein such API-containing LNP are produced in a single mixing step.

According to exemplary embodiments, the present invention provides a device for preparing liposomes encapsulating an API that includes a manifold that may have a mixing chamber, at least one lipid solution inlet port connected to the chamber; and a plurality of aqueous solution inlet ports connected to the chamber.

Another embodiment of the invention provides for a process for preparing liposomes that encapsulate an active pharmaceutical ingredient (API) that may include a step of providing, (i) a lipid solution that may include an organic solvent and a lipid, in a lipid solution reservoir, and (ii) an aqueous solution comprising water and a buffer, in an aqueous solution reservoir; and a step of providing a manifold that that may include (i) a mixing chamber; (ii) at least one lipid solution inlet port connected to the chamber; and, (iii) a plurality of aqueous solution inlet ports connected to the chamber; a step of mixing the lipid solution and the aqueous solution, as a stream of each solution is introduced into the mixing chamber, to produce liposomes; and a step of encapsulating the active pharmaceutical ingredient within the liposomes.

In an alternative embodiment, the invention provides liposomes made by the process of the invention.

The invention also provides liposomes, wherein the liposomes encapsulate an API, and the average diameter of the liposome is about 10-300 nm.

This invention enables control of LNP size, size distribution, morphology, and manufacturing scale by altering the port size, number and geometry of the manifold, and by selecting the flow rate or flow velocity of the lipid and aqueous solutions. These and other advantages of the present technology will be apparent when reference is made to the accompanying drawings and the following description.

BRIEF DESCRIPTION OF THE DRAWINGS

FIG. 4A, FIG. 4B, FIG. 4C and FIG. 4D show the effect of flow rate and manifold pore size on liposome particle size for a 5-port manifold with pore sizes of 1 mm (FIG. 4A and FIG. 4B) and 1.6 mm (FIG. 4C and FIG. 4D).

DETAILED DESCRIPTION

Figure 1B:
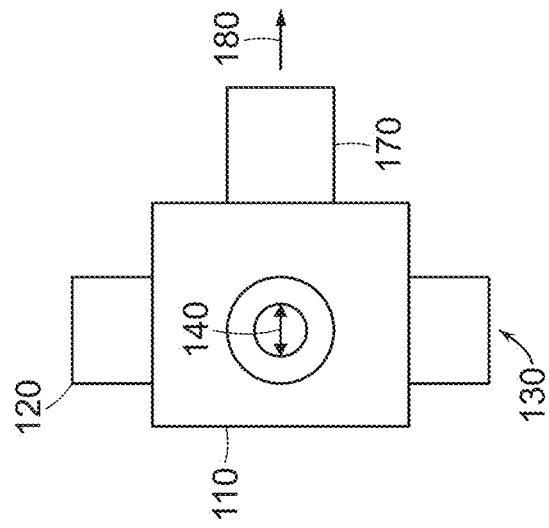
FIG. 1A and FIG. 1B illustrate projections from the top (FIG. 1A) and side (FIG. 1B) of an exemplary 5-port manifold for preparing liposomes encapsulating an API.

While this invention is susceptible of embodiments in many different forms, there are shown in the drawings and will herein be described in detail several specific embodiments with the understanding that the present disclosure is to be considered as an exemplification of the principles of the technology and is not intended to limit the invention to the embodiments illustrated.

Definitions

The term "flow rate" refers to the volume of a lipid solution or an aqueous solution fed to an inlet port.

Term "flow velocity" refers to the liquid flow speed in the inlet port, for example, calculated as V=R/6000 A, where V (m/s) is the flow velocity, R (ml/min) is the flow rate, A (cm$^2$) is the cross section area of the pore of an inlet port.

The term "lipid nanoparticles," or LNP, refers to liposomes (e.g., unilamellar or multilamellar), solid lipid particles or lipid discs. Exemplary liposomes and lipid discs are shown in the Examples.

The term of "cationic lipid" refers to a lipid that carries a net positive charge at about pH 3-pH 9.

As used herein the term of "anionic lipid" refers to a lipid or a cholesterol derivative that carries a net negative charge at about pH 3-pH 9.

The term "pegylated lipid" refers to a lipid that is conjugated with a polyethylene glycol polymer.

The term "neutral lipid" refers to the lipid that does not carry net charge at about pH 3-pH 9.

The term of "lipid-anchored molecule" refers to a molecule that has a lipid or cholesterol anchor and thus may be incorporated into a liposome.

The term of "active pharmaceutical ingredient" or API refers to a pharmaceutical active ingredient that is used for disease treatment or for disease prevention (vaccine). API may also refer to an ingredient intended for disease diagnosis.

Figure 1A:
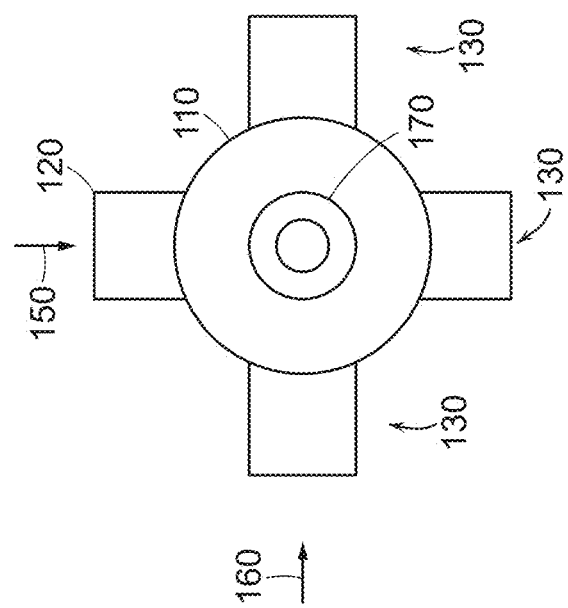

FIG. 1 A and FIG. 1B, illustrate an embodiment of the invention. A five-port manifold is shown having one lipid solution inlet port, three aqueous solution inlet ports and one liposome outlet port. FIG. 1 A, is a projection from the top of the manifold, while FIG. 1 B, is a projection from the side of the manifold. FIG. 1A and FIG. 1B show that manifold mixing chamber 110 is connected to one lipid solution inlet port 120, through which the lipid solution enters the mixing chamber. Three aqueous solution inlet ports 130 are also connected to the mixing chamber, and provide passage of the aqueous solution to enter the chamber. This figure illustrates that lipid solution inlet port and the aqueous solution inlet ports may have an inner diameter indicated by 140. Lipid solution 150 enters into the lipid solution inlet port while aqueous solution 160 passes into the aqueous solution inlet ports and the LNP 180 exit LNP outlet port 170.

Figure 2:
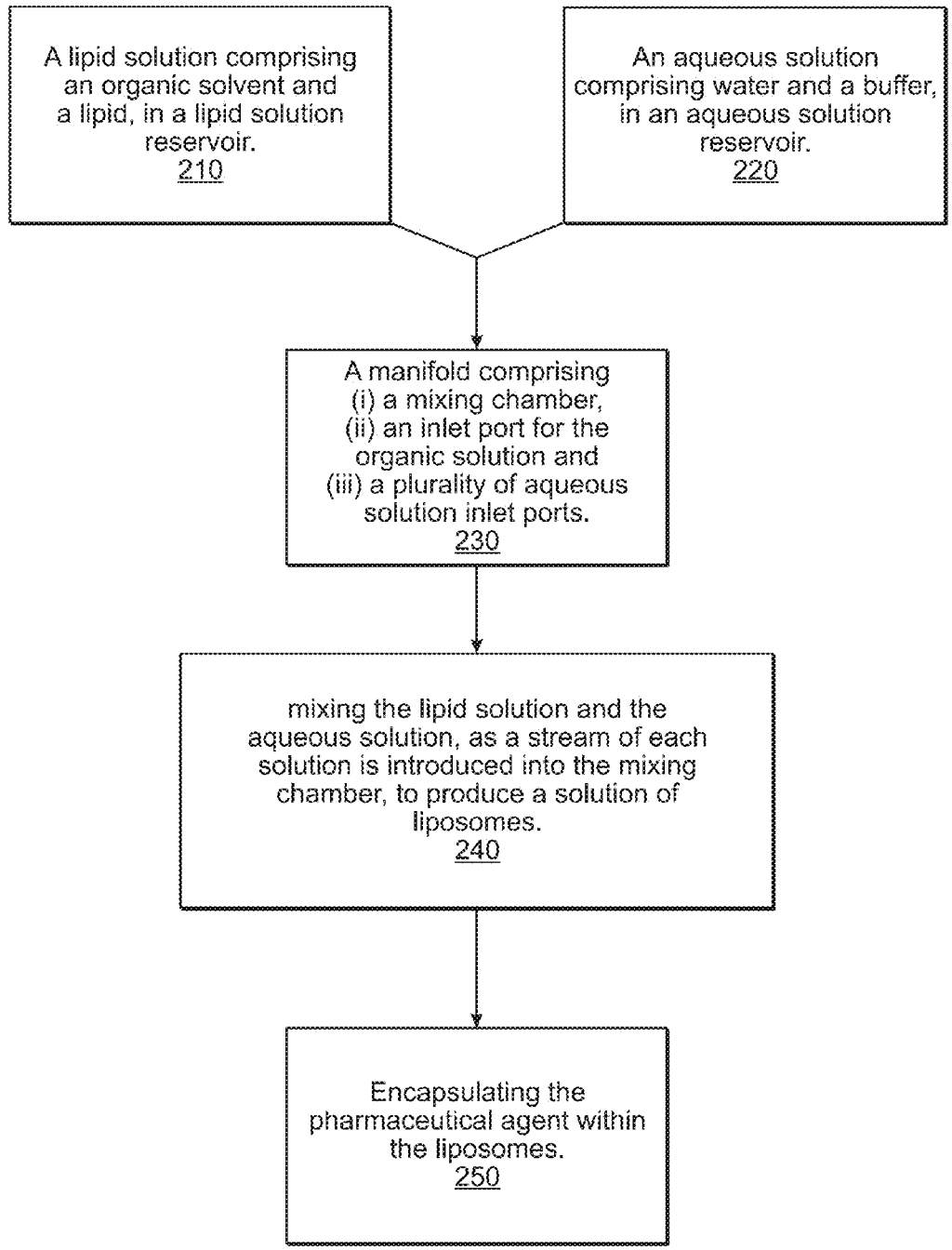
FIG. 2 shows a flowchart of an exemplary process for preparing liposomes encapsulating an API.

FIG. 2 is a flow chart that illustrates an exemplary process that may be used to implement an embodiment of the present technology. As shown in FIG. 2, the flow chart provides for lipid solution 210 that includes an organic solvent and a lipid, and aqueous solution 220 that includes water and a buffer. The lipid solution or the aqueous solution may further include a solubilized API. The lipid solution and the aqueous solution may simultaneously enter the mixing chamber of manifold 230. In some embodiments one, or the other or both solutions have a positive pressure, which may be provided by a pump apparatus. The lipid solution and the aqueous solution are mixed in the mixing chamber to produce a solution of LNP 240. The process of the invention also provides for a step of encapsulating the API within the LNP. When an API is solubilized in either the lipid solution or the aqueous solution, the step of encapsulating the API may occur during formation of the LNP in the mixing chamber. In other embodiments, the API may be incorporated into the LNP by diffusion of the agent from outside the liposome. In some embodiments, the methods of the invention comprises step c) of loading LNP recovered from the LNP solution with an API.

Figure 3:
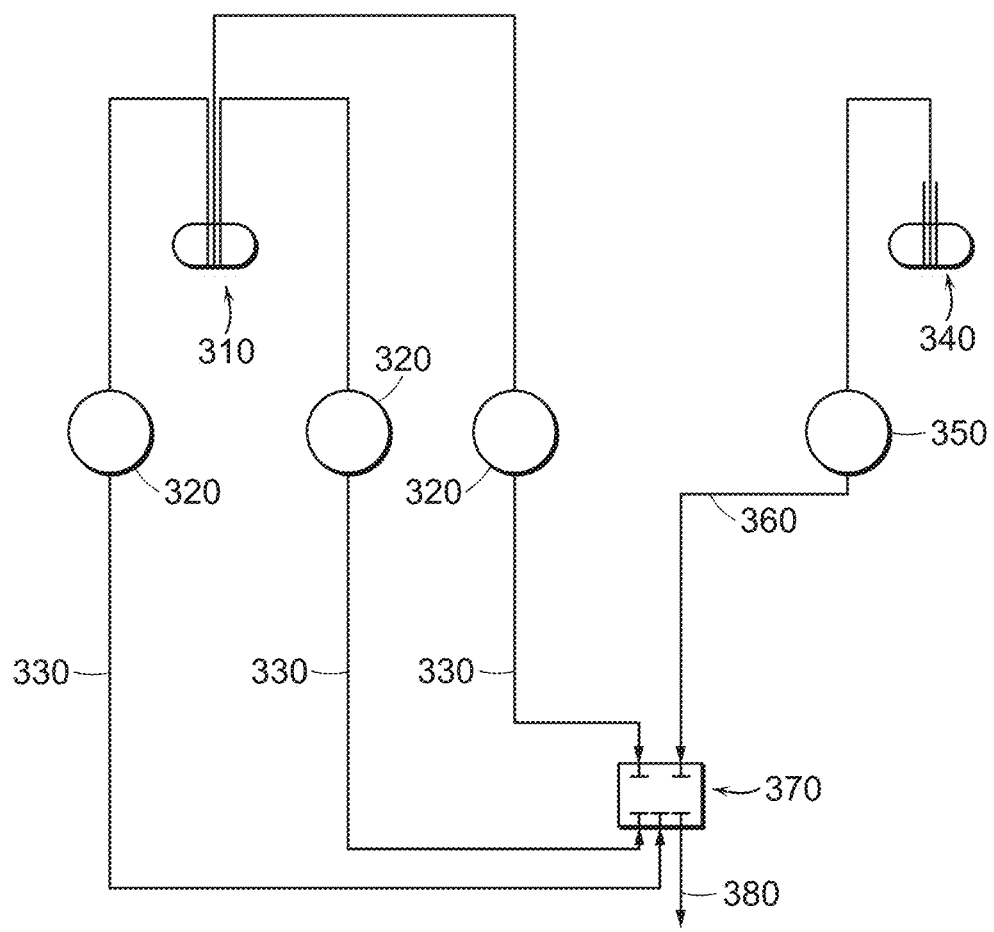
FIG. 3 is schematic representation of an embodiment of the invention in which an insoluble API is encapsulated with liposomes made with a 5-port exemplary manifold.

FIG. 3 shows a schematic representation of one embodiment of the invention in which a water insoluble API is dissolved in the lipid solution. An aqueous solution in reservoir 310 may be conveyed to manifold 370 through conduits 330. Simultaneously, a lipid solution containing the solubilized API in reservoir 340 maybe conveyed to manifold 370, through conduit 360. Pumps 320 and 350 may be used to adjust and monitor the flow rate of each solution. The aqueous solution enters the manifold through the aqueous solution inlet ports, and the lipid solution enters the manifold through the lipid solution inlet port, shown previously in FIG. 1A and FIG. 1B. The mixing of the aqueous and the lipid solution in the manifold results in the formation of lipid nanoparticles 380 which exit the manifold through the lipid nanoparticle outlet port, as shown in FIG. 1A and FIG. 1B.

FIG. 4 A and FIG. 4B show results for liposomes containing doxorubicin HCl manufactured using a 5-port manifold having inlet and outlet ports 1 mm in diameter. At a flow rate of 1 ml/min the liposomes have an average diameter of about 150 nm. As the flow rate increases, the diameter of the liposomes decreases, until it reaches a plateau of about 50 nm when the flow rate is from 20 to 50 ml/min. Graph B shows that the polydispersity index ("PDI"), a measure of particle size distribution, is about 0.2 at a flow rate from 20 to 50 ml/min. The PDI increases to about 0.3 when the flow rate is below 10 ml/min. FIG. 4 C and FIG. 4D show results for liposomes manufactured with a 5-port manifold having ports of 1.6 mm in diameter. Panel C shows that at a flow rate of 5 ml/min, the liposomes have an average diameter of about 120 nm. There is an approximately linear decrease in diameter as the flow rate increases up to 60 ml/min. Panel D shows that the PDI of 0.35 is relatively independent of flow rate.

Figure 5:
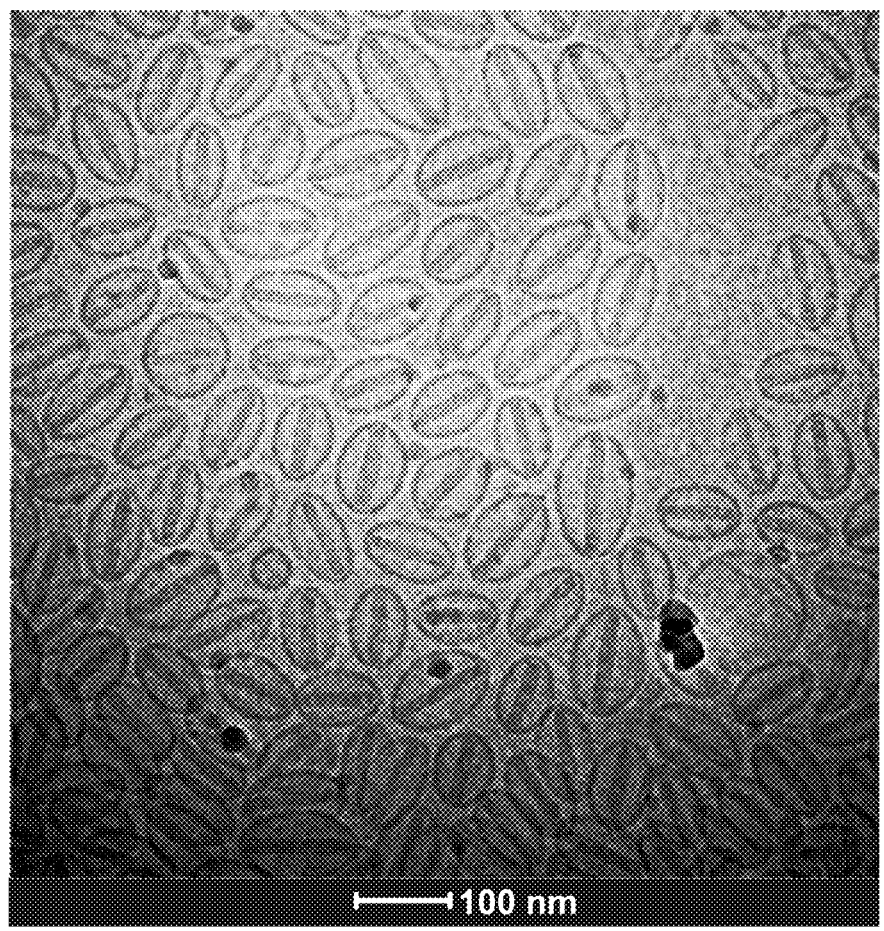
FIG. 5 is a Cryo-TEM image of liposomes made with a 5-port exemplary manifold and loaded with doxorubicin.

FIG. 5 shows Cryo-TEM imaging of liposomes loaded with doxorubicin. The liposome was made by a 5-port manifold having ports 1.0 mm in diameter. The formulation is substantially the same as Doxil which is a clinically used formulation of the anticancer liposome drug, doxorubicin. As shown in the figure, lipids form unilamellar liposomes, in which doxorubicin forms crystals inside.

Figure 6A:
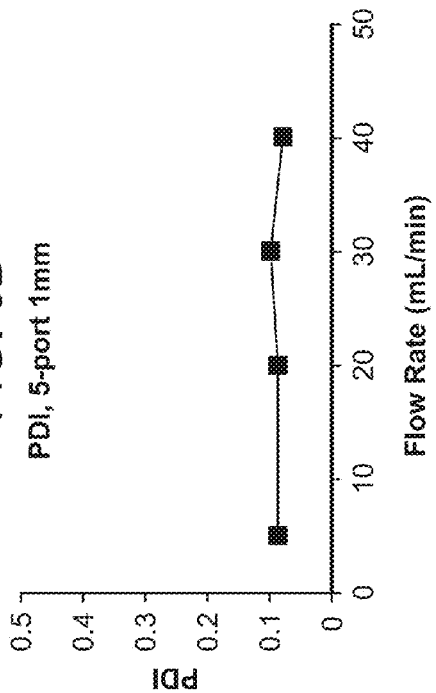
FIG. 6A, FIG. 6B, FIG. 6C and FIG. 6D show the effect of flow rate and manifold pore size on the size (FIG. 6A and FIG. 6C), polydispersity index (FIG. 6B and FIG. 6D) of siRNA liposomes, and Cryo-TEM image (FIG. 6E) of the liposomes.
Figure 6B:
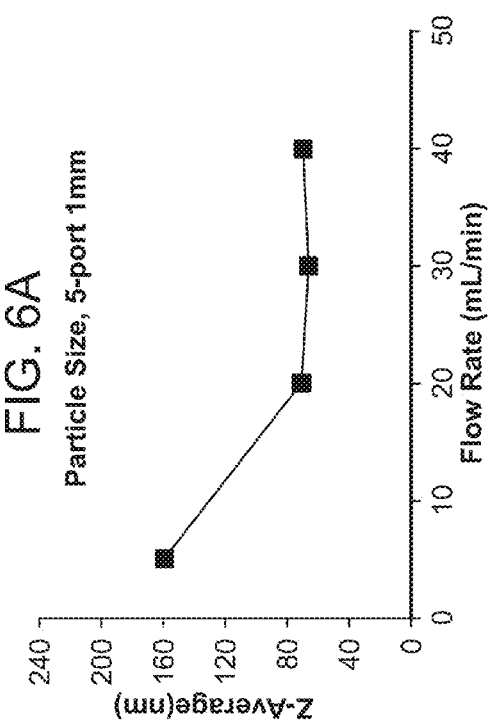
Figure 6C:
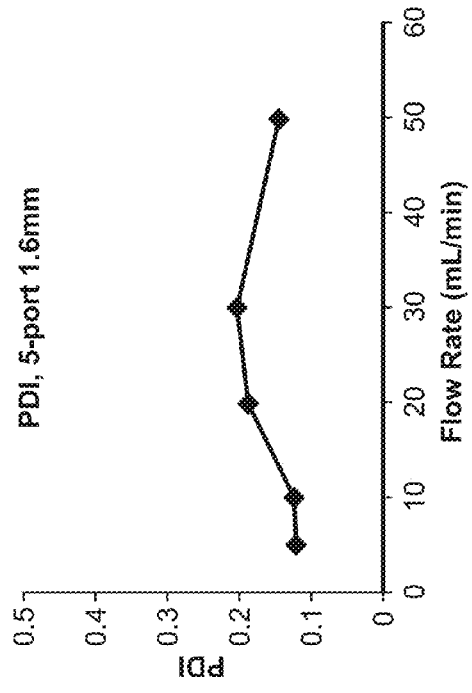
Figure 6D:
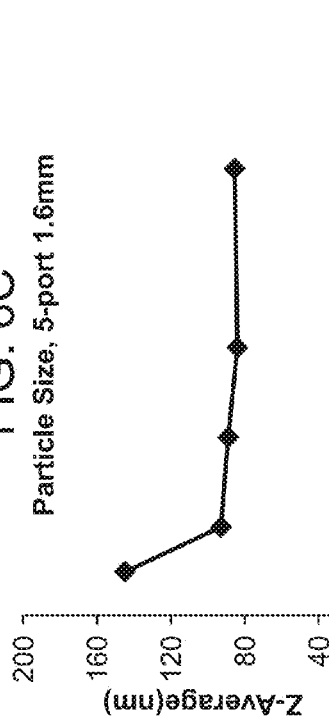
Figure 6E:
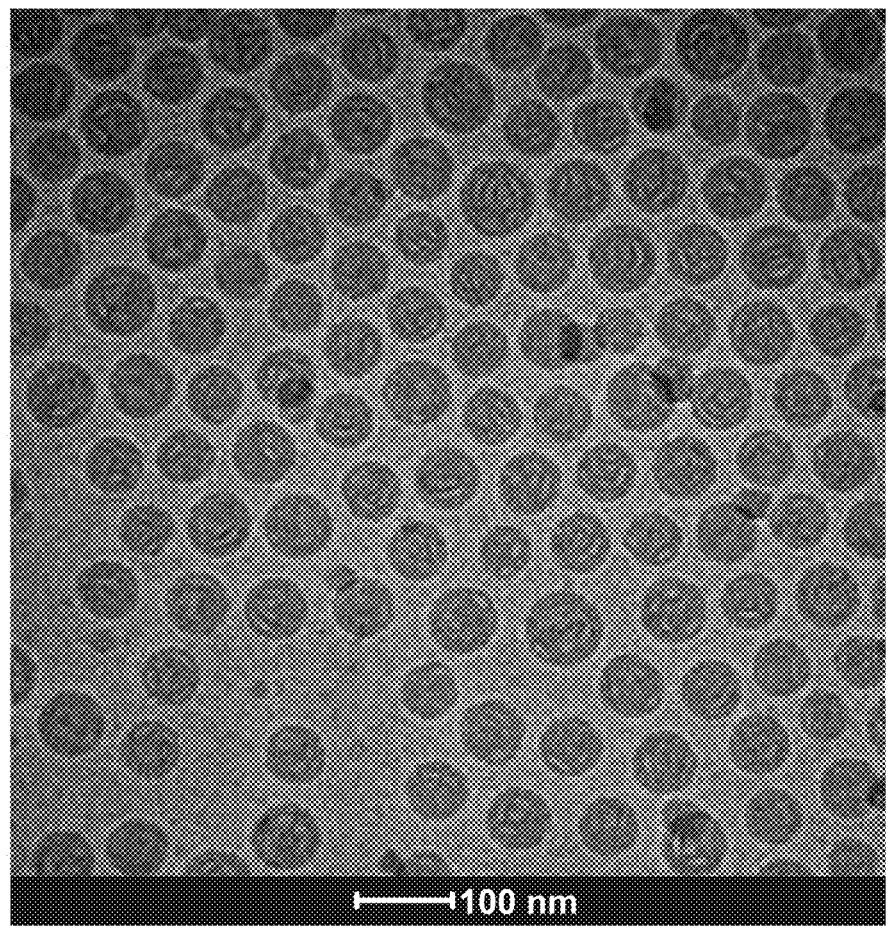

FIG. 6 A, FIG. 6B, FIG. 6C and FIG. 6D show the results obtained for liposomes containing siRNA. FIG. 6 A and FIG. 6B illustrate the results for liposomes manufactured with a 5-port manifold having ports 1 mm in diameter. At a flow rate of 5 ml/min the liposomes have an average diameter of about 160 nm. The diameter of the liposomes decreases when the flow rate is 20 ml/min and does not change substantially as the rate is further increased. The PDI of 0.008 is relatively independent of flow rate. FIG. 6C and FIG. 6D illustrate the results for liposomes manufactured with a 5-port manifold having ports 1.6 mm in diameter. FIG. 6C shows that a flow rate of 5 ml/min the liposomes have an average diameter of about 150 nm. The size decreases to about 90 nm when the flow rate increases to 10 ml/min. A further increase in flow rate does not result in a substantial change in the size of the nanoparticle. FIG. 6D shows the PDI is about 0.1-0.2 in the range of flow rate from 5 to 50 ml/min. FIG. 6E shows the Cryo-TEM images of siRNA liposomes. As can be seen from the figure, the particle size is homogenous, while the morphology is not unilamellar or multilamellar.

Figure 7A:
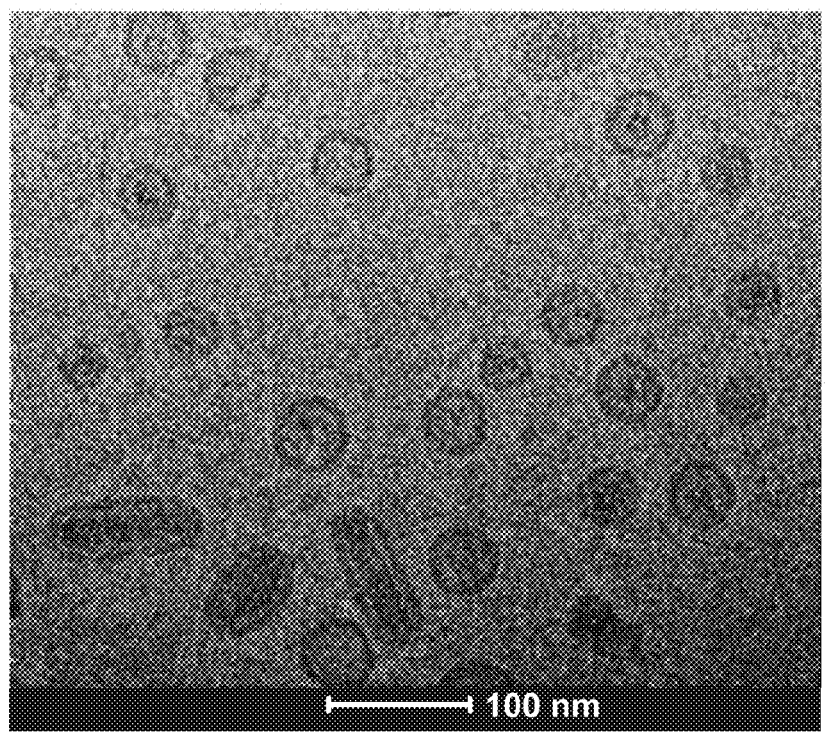
FIG. 7A shows a Cryo-TEM image of unilamellar liposomes generated at a flow rate of 40 ml/min.
Figure 7B:
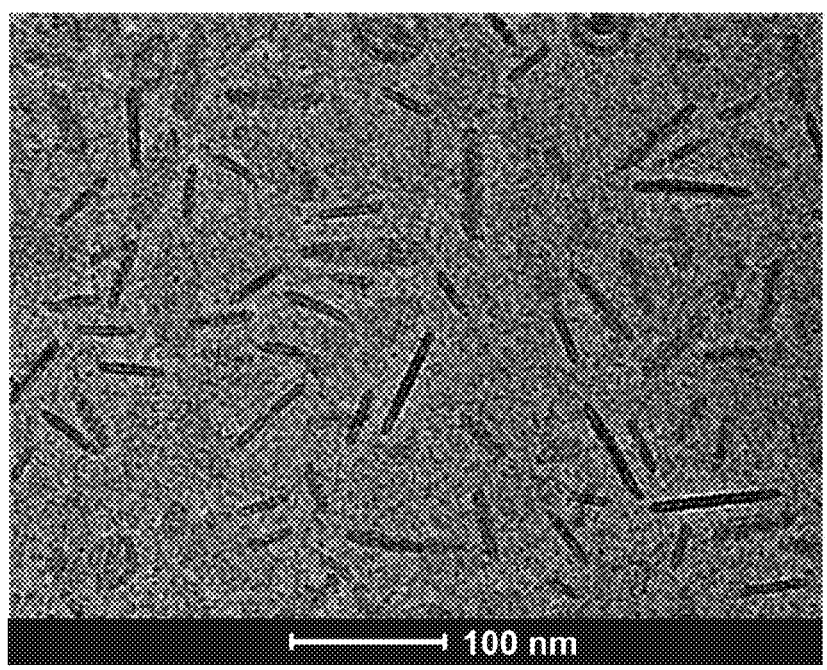
FIG. 7B shows a Cryo-TEM image of lipid discs generated at a flow rate of 5 ml/min.

FIGS. 7A-7B show the effect of flow rate on the morphology of the lipid particles. FIG. 7A shows a Cryo-TEM image of unilamellar liposomes generated at a flow rate of 40 ml/min (pore size 1 mm; 5-port manifold), which produced particle with a diameter of 81.1 nm and PDI of 0.021. The crystals inside the liposomes are the loaded doxorubicin. FIG. 7B shows a Cryo-TEM image of lipid discs generated at a flow rate of 5 ml/min (pore size 1 mm; 5-port manifold), which produced predominantly generated lipids discs with about 60 nm in diameter and about 6 nm in lipid bilayer thickness.

FIGS. 8A-8D show alternative exemplary embodiments for the number and orientation of inlets and outlets in a 7-port manifold of the invention, which was used in Example 8. Arrows indicate the direction of flow in the ports, while the blunted lines indicate sealed unused ports in a prefabricated manifold.

A Device for Preparing Liposomes Encapsulating an Active Pharmaceutical Agent

The invention provides a device adapted to perform the method of the invention, such as a manifold system described herein.

In some aspects, the present technology provides a device for preparing LNP encapsulating an API that includes a manifold that may have a mixing chamber, at least one lipid solution inlet port connected to the chamber; and a plurality of aqueous solution inlet ports connected to the chamber.

In a preferred embodiment, the device may include a LNP solution outlet port connected to the chamber.

Preferably, the device may include a reservoir for a lipid solution which is connected to the lipid solution inlet port by a lipid solution conduit, and a reservoir for an aqueous solution which is connected to the aqueous solution inlet ports by an aqueous solution conduit.

The inlet ports for the lipid and aqueous solutions, and the exit port for the liposome solutions may have an internal diameter which is the same or different. Preferably inlet and outlet ports have an internal diameter from about 0.1 mm to about 10 mm. More preferably the ports have an internal diameter from about 0.15 mm to about 5 mm.

Figure 8D:
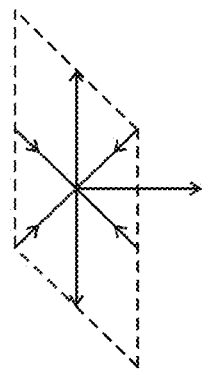
FIG. 8C and FIG. 8D show alternative exemplary embodiments for the number and orientation of inlets and outlets in a 7-port manifold of the invention, with 1 outlet port.
Figure 8C:
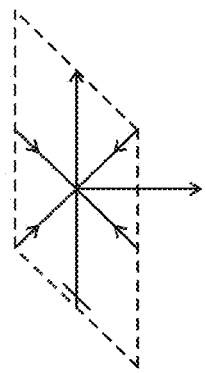
Figure 8B:
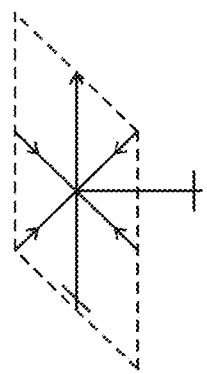
FIG. 8B shows alternative exemplary embodiments for the number and orientation of inlets and outlets in a 7-port manifold of the invention, with 2 outlet ports.
Figure 8A:
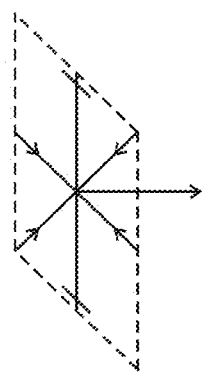
FIG. 8A shows alternative exemplary embodiments for the number and orientation of inlets and outlets in a 7-port manifold of the invention, with 3 outlet ports.

In some embodiments, the mixing chamber is located at the point of conversion of the conduits and may itself be formed by two or more conduits passing through each other, or intersecting, without any change in the shape of the conduits. For instance, the mixing chamber can formed by drilling in a solid material two or more pass-through channels all intersecting at the point of conversion. In addition, one or more conduits may be sealed so that there is no passage of fluid permitted through the conduit. Such seal may be located either immediately prior to the point of intersection or distantly therefrom. For example, sealed conduits are illustrated in FIGS. 8A, 8C and 8D.

In some embodiments, one manifold may contain more than one mixing chamber. For example, one set of inlet ports intersect at one chamber, and another group of inlet ports intersect at another chamber, and the two chambers are connected by conduits to the third mixing chamber that is connected to an outlet port.

Preferably, a pump is used to induce a positive flow to the lipid solution and to the aqueous solution. The pump may be an inline pump or a syringe pump.

Typically, the mixing chamber may be connected to 2 to about 20 aqueous solution inlet ports. Preferably, there may be from 3 to about 11 such ports, from 3 to about 12 such ports. More preferably, there are from 3 to about 10, or from 3 to about 7 aqueous solution entry inlet ports. The mixing chamber may also be connected to from 1 to about 5 lipid solution inlet ports. Preferably, there are from 1 to about 3 lipid solution inlet ports. Most preferably, there is 1 or 2 lipid solution inlet ports. In a preferred embodiment, the mixing chamber is connected to at least 1 (e.g., 1, 2, 3, 4, or 5) lipid solution port(s) and at least 2 (e.g., 2, 3, 4, 5, 6, 7, 8, 9, 10, 11, 12, 13, 14, 15, 16, 17, 18, 19 or 20) aqueous solution inlet ports.

The mixing chamber is further connected to 1 to about 3 outlet ports for the liposome solution for particle size control, preferably, there is 1 (e.g., 1, 2, or 3) outlet port(s).

In certain aspects, the angle between the inlet ports for the lipid and aqueous solutions is from about 18° to about 180°. Preferably the angel may be from about 24° to about 180°, more preferably from about 30° to about 180°. In some embodiments, the angle between at least one lipid and at one aqueous solution inlet ports is not 180° or a substantially similar angle. For example, the angle between at least one lipid and at one aqueous solution inlet ports is about 120° or less, about 90° or less, for example, as shown in FIGS. 8A-8D. The angle between ports is the angle at which streams of respective solutions are directed into the mixing chamber.

The lipid and aqueous solutions may have the same flow rate through the manifold. Alternatively, the solutions may have different flow rates. The flow rates for the lipid and aqueous solutions may be 1 ml/min to about 6,000 ml/min, e.g., from about 1 ml/min to about 1,500 ml/min. Preferably, the flow rates may be from about 5 ml/min to about 1,000 ml/min, e.g., from about 5 ml/min to about 400 ml/min. More preferably, the rates may be the rates may be from about 20 ml/min to about 600 ml/min or from about 10 ml/min to about 300 ml/min. In some embodiments, the flow rates are adjusted based on the size of inlet ports to obtain the desired LNP size, morphology, PDI, and manufacturing scale.

Process for Preparing LNP

The invention provides a method for preparing lipid nanoparticles (LNP), the method comprising:

a) introducing i) one or more streams of a lipid solution via a first set of one or more inlet ports of a manifold and ii) one or more streams of an aqueous solution via a second set of one or more an inlet ports of the manifold, thereby mixing the lipid solution and the aqueous solution so as to produce an LNP solution; and b) recovering the LNP solution via one or more outlet ports of the manifold;

wherein the angle between at least one lipid and at one aqueous solution inlet ports is not 180° or a substantially similar angle. In some aspects, at least one stream of lipid solution and at one stream of aqueous solution collide at an angle less than about 180°. Thus, in some aspects, the method does not include a T-connector.

In some embodiments, the angle between at least one lipid and at one aqueous solution inlet ports is about 120° or less, e.g., 115° or less, 100° or less, 90° or less, 80° or less, 72° or less, 60° or less, 45° or less, 30° or less, 18° or less, In some embodiments, the aqueous solution in step ii) is introduced via at least two inlet ports, e.g., at least 3, 4, 5, 6, 7, 8, 9, 10, 11, 12, 13, 14, 15, 16, 17, 18, 19, 20 or more. In some embodiments, the aqueous solution in step ii) is introduced via at least 3 but no more than 11 inlet ports, e.g., at least 3 but not more than 7, at least 3 but no more than 5, at least 4 but no more than 11, at least 5 but no more than 11, at least 6 but no more than 11.

In some embodiments, at least two (e.g., 3, 4, 5, 6, 7, etc.) aqueous inlet ports and at least one (e.g., 2, 3, 4, 5, etc.) lipid solution inlet port are in the same plane.

In some embodiments, at least one (e.g., 2) outlet port is substantially perpendicular to the plane of inlet ports. In other embodiments, at least one (e.g., 2, 3, 4, 5, etc.) outlet port is substantially not perpendicular to the plane of inlet ports.

In some embodiments, at least two (e.g., 3, 4, 5, 6, 7, etc.) aqueous solution inlet ports and at least one (e.g., 2, 3, 4, 5, etc.) lipid solution inlet port are not in the same plane.

In some embodiments, the aqueous solution introduced into at least one of the inlet ports differs from a second aqueous solution introduced into another inlet port.

In some embodiments, the aqueous solution and/or the lipid solution comprises an active pharmaceutical ingredient (API).

In some embodiments, step a) further comprises introducing iii) one or more streams of non-aqueous solutions via one or more inlet ports of the manifold.

Another embodiment of the invention provides for a process for preparing LNP that encapsulate an active pharmaceutical ingredient (API) that may include a step of providing (i) a lipid solution that may include an organic solvent and a lipid, in a lipid solution reservoir, and (ii) an aqueous solution comprising water and a buffer, in an aqueous solution reservoir; and a step of providing a manifold that that may include (i) a mixing chamber; (ii) at least one lipid solution inlet port connected to the chamber; and, (iii) a plurality of aqueous solution inlet ports connected to the chamber; a step of mixing the lipid solution and the aqueous solution, as a stream of each solution is introduced into the mixing chamber, to produce LNP; and a step of encapsulating the active pharmaceutical ingredient within the LNP.

In one embodiment of the process, the lipid solution may include the API to be encapsulated. In another embodiment, the aqueous solution may include the API.

The step of encapsulating the drug into a liposome may occur at the same time as the mixing step when the drug is solubilized in the lipid or aqueous solution. While not being bound by theory it is believed that the LNP form instantly when the aqueous solution and the lipid solution make contact. An API, carried by the lipid solution or by the aqueous solution, may be encapsulated in the LNP through either lipophilic interaction, or electrostatic interaction, or both, between the API and the lipids.

Alternatively the API may be introduced into empty LNP by a diffusion or another loading process as illustrated in FIG. 2.

An exemplary manifold of the process is described above and shown in FIG. 1A and FIG. 1B The Lipid and Aqueous Solutions The invention utilizes lipid and aqueous solutions. The lipid solution may comprise an organic solvent. The organic solvent may be a water miscible solvent. Preferably, the water miscible solvent is selected from the group consisting of ethanol, methanol, DMSO and isopropanol. Most preferably, the organic solvent is ethanol.

The lipid solution may include a mixture of lipids. The mixture of lipids preferably includes cholesterol.

The mixture of lipids may also include a cationic lipid. The cationic lipid may be, but is not limited to, N,N-dioleyl-N,N-dimethylammonium chloride ("DODAC"); N-(2,3-dioleyloxy)propyl)-N,N,N-trimethylammonium chloride ("DOTMA"); N-(2,3-dioleyloxy)propyl)-N,N-dimethylammonium chloride ("DODMA"); N,N-distearyl-N,N-dimethylammonium bromide ("DDAB"); N-(2,3-dioleoyloxy)propyl)-N,N,N-trimethylammonium chloride ("DOTAP"); N-(2,3-dioleoyloxy)propyl)-N,N-dimethylammonium chloride ("DODAP"); 3-(N—(N',N'-dimethylaminoethane)carbamoyl)cholesterol ("DC-Chol"); N-(1,2-dimyristyloxyprop-3-yl)-N,N-dimethyl-N-hydroxyethyl ammonium bromide ("DMRIE"); 1.2-dilinoleyloxy-N,N-dimethyl-3-aminopropane (DLinDMA); 1,2-distearyloxy-N,N-dimethyl-3-aminopropane (DSDMA); 1.2-dilinolenyloxy-N,N-dimethyl-3-aminopropane (DLenDMA); 2-{4-[(3b)-cholest-5-en-3-yloxy]butoxy}-N,N-dimethyl-3-[(9Z,12Z)-octadeca-9,12-dien-1-yloxy]propan-amine (CLinDMA).

In some embodiments the mixture of lipids may include an anionic lipid. The anionic lipid may be but are not limited to diacylglycerol phophatidic acid (1,2-distearoyl-sn-glycero-3-phosphate (DSPA); 1,2-dipalmitoyl-sn-glycero-3-phosphate (DPPA); 1,2-dimyristoyl-sn-glycero-3-phosphate (DMPA); 1,2-dilauroyl-sn-glycero-3-phosphate (DLPA); 1,2-dioleoyl-sn-glycero-3-phosphate (DOPA)), diacylglycerol phosphoglycerol (1,2-distearoyl-sn-glycero-3-phospho-(1'-rac-glycerol) (DSPG); 1,2-dipalmitoyl-sn-glycero-3-phospho-(1'-rac-glycerol) (DPPG); 1,2-dimyristoyl-sn-glycero-3-phospho-(1'-rac-glycerol) (DMPG); 1,2-dilauroyl-sn-glycero-3-phospho-(1'-rac-glycerol) (DLPG); 1,2-dioleoyl-sn-glycero-3-phospho-(1'-rac-glycerol) (DOPG)), phosphatidylglycerol, cardiolipin, diacylphosphatidylserine, N-succinyl phosphatidylethanolamines, N-glutarylphosphatidylethanolamines, lysylphosphatidylglycerols, and other anionic modifying groups joined to neutral lipids. The mixture of lipids may also include a neutral lipid. The neutral lipids may be but are not limited to diacylglycerol phosphocholine (L-α-phosphatidylcholine, hydrogenated (Soy) (HSPC); 1,2-distearoyl-sn-glycero-3-phosphocholine (DSPC); 1,2-dipalmitoyl-sn-glycero-3-phosphocholine (DPPC); 1,2-dimyristoyl-sn-glycero-3-phosphocholine (DMPC); 1,2-dilauroyl-sn-glycero-3-phosphocholine (DLPC); 1,2-dioleoyl-sn-glycero-3-phosphocholine (DOPC), diacylglycerol phosphoethanolamine (1,2-distearoyl-sn-glycero-3-phosphoethanolamine (DSPE); 1,2-dipalmitoyl-sn-glycero-3-phosphoethanolamine (DPPE); 1,2-dimyristoyl-sn-glycero-3-phosphoethanolamine (DMPE); 1,2-dilauroyl-sn-glycero-3-phosphoethanolamine (DLPE); 1,2-dioleoyl-sn-glycero-3-phosphoethanolamine (DOPE), and phosphatidylserine.

The mixture of lipids may also include a pegylated lipid. The pegylated lipid may be but are not limited to 1,2-distearoyl-sn-glycero-3-phosphoethanolamine-N-[methoxy(polyethylene glycol)-2000] (mPEG-2000-DSPE); 1,2-dioctadecanoyl-sn-glycero-3-phosphoethanolamine-N-[methoxy(polyethylene glycol)-2000] (mPEG-2000-DOPE); 1,2-dipalmitoyl-sn-glycero-3-phosphoethanolamine-N-[methoxy(polyethylene glycol)-2000] (mPEG-2000-DPPE); 1,2-dimyristoyl-sn-glycero-3-phosphoethanolamine-N-[methoxy(polyethylene glycol)-2000] (mPEG-2000-DMPE); 1,2-dilauroyl-sn-glycero-3-phosphoethanolamine-N-[methoxy(polyethylene glycol)-2000] (mPEG-2000-DLPE); 1,2-distearoyl-sn-glycero-3-phosphoethanolamine-N-[methoxy(polyethylene glycol)-5000] (mPEG-5000-DSPE); 1,2-dioctadecanoyl-sn-glycero-3-phosphoethanolamine-N-[methoxy(polyethylene glycol)-5000] (mPEG-5000-DOPE); 1,2-dipalmitoyl-sn-glycero-3-phosphoethanolamine-N-[methoxy(polyethylene glycol)-5000] (mPEG-5000-DPPE); 1,2-dimyristoyl-sn-glycero-3-phosphoethanolamine-N-[methoxy(polyethylene glycol)-5000] (mPEG-5000-DMPE); 1,2-dilauroyl-sn-glycero-3-phosphoethanolamine-N-[methoxy(polyethylene glycol)-5000] (mPEG-5000-DLPE).

The mixture of lipids may also include a lipid-like molecule or lipidoid. The mixture of lipid may also include a lipid- or cholesterol-conjugated molecule including a protein, or a peptide, or an oligonucleotide.

The aqueous solution of the process preferably includes water and a buffer. Buffers may be of but are not limited to phosphate, histidine, HEPES, Tris, acetate, and citrate.

Active Pharmaceutical Ingredient

Preferably, the API may be an anticancer agent, an anti-inflammatory agent, and an anti-diabetic agent, an anti-fungal agent and an antibiotic agent.

The API may be a polynucleotide (including an oligonucleotide) a protein or a small molecule.

In one embodiment the API is a polynucleotide. The polynucleotide may be a genomic DNA fragment, cDNA, mRNA, ssRNA, dsRNA, microRNA, siRNA, shRNA, sdRNA, DsiRNA, LNA, and antisense DNA or RNA.

Alternatively, the API may be a small organic molecule API. Preferably, the molecule has a molecular weight from about 1500 g/mole to about 50 g/mole.

An API can be, for example, an anticancer agent, an antibiotic agent, an antiviral agent, an anti-fungal agent, or an analgesic.

Exemplary anticancer agents that may include but are not limited acivicin, aclarubicin, acodazole, ametantrone, aminoglutethimide, anthramycin, asparaginase, azacitidine, azetepa, bisantrene, bleomycin, busulfan, cactinomycin, calusterone, caracemide, carboplatin, carmustine, carubicin, chlorambucil, cisplatin, cyclophosphamide, cytarabine, dacarbazine, dactinomycin, daunorubicin, dezaguanine, diaziquone, docetaxel, doxorubicin, epipropidine, erlotinib, etoposide, etoprine, floxuridine, fludarabine, fluorouracil, fluorocitabine, hydroxyurea, iproplatin, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, paclitaxel, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, teniposide, teroxirone, thiamiprine, thioguanine, tiazofurin, triciribine phosphate, triethylenemelamine, trimetrexate, uracil mustard, uredepa, vinblastine, vincristine, vindesine, vinepidine, vinrosidine, vinzolidine, zinostatin and zorubicin.

Exemplary antibiotic agents that may include but are not limited to aminoglycoside; amikacin; gentamicin; kanamycin; neomycin; netilmicin; steptomycin; tobramycin; ansamycins; geldanamycin; herbimycin; carbacephem; loracarbef; carbacepenem; ertapenem; doripenem; imipenem/cilastatin; meropenem; cephalosporin; cefadroxil; cefazolin; cefalotin or cefalothin; cefalexin; cefaclor; cefamandole; cefoxitin; cefprozil; cefuroxime; cefixime; cefdinir; cefditoren; cefoperazone; cefotaxime; cefpodoxime; ceftazidime; ceftibuten; ceftizoxime; ceftriaxone; cefepime; ceftobiprole; glycopeptide; teicoplanin; vancomycin; macrolides; azithromycin; clarithromycin; dirithromycin; erythromycin; roxithromycin; troleandomycin; telithromycin; spectinomycin; monobactam; aztreonam; penicillins; amoxicillin; ampicillin; azlocillin; carbenicillin; cloxacillin; dicloxacillin; flucloxacillin; mezlocillin; meticillin; nafcillin; oxacillin; penicillin, piperacillin, ticarcillin; bacitracin; colistin; polymyxin B; quinolone; ciprofloxacin; enoxacin; gatifloxacin; levofloxacin; lomefloxacin; moxifloxacin; norfloxacin; ofloxacin; trovafloxacin; sulfonamide; mafenide; prontosil (archaic); sulfacetamide; sulfamethizole; sufanilimide (archaic); sulfasalazine; sulfisoxazole; trimethoprim; trimethoprim-sulfamethoxazole (co-trimoxazole) (TMP-SMX); tetracycline; demeclocycline; doxycycline; minocycline; oxytetracycline; tetracycline; arsphenamine; chloramphenicol; clindamycin; lincomycin; ethambutol; fosfomycin; fusidic acid; furazolidone; isoniazid; linezolid; metronidazole; mupirocin; nitrofuantoin; platensimycin; purazinamide; quinupristin/dalfopristin; rifampin or rifampicin; and timidazole. In specific embodiments, the anti-cancer agent is chosen from daunorubicin, doxorubicin, paclitaxel, docetaxel, cisplatin, carboplatin, cytarabine, floxuridine, fludarabine, fluorouracil, iproplatin, leuprolide acetate, and methotrexate.

Exemplary antiviral agent that may include, but are not limited to thiosemicarbazone; metisazone; nucleoside and/or nucleotide; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivative; foscamet; fosfonet; protease inhibitor; saquinavir; indinavir; ritonavir; nelfinavir; amprenavir; lopinavir; fosamprenavir; atazanavir; tipranavir; nucleoside and nucleotide reverse transcriptase inhibitor; zidovudine; didanosine; zalcitabine; stavudine; lamivudine; abacavir; tenofovir disoproxil; adefovir dipivoxil; emtricitabine; entecavir; non-nucleoside reverse transcriptase inhibitor; nevirapine; delavirdine; efavirenz; neuraminidase inhibitor; zanamivir; oseltamivir; moroxydine; inosine pranobex; pleconaril; and enfuvirtide.

Exemplary anti-fungal agent that may include but are not limited to allylamine; terbinafine; antimetabolite; flucytosine; azole; fluconazole; itraconazole; ketoconazole; ravuconazole; posaconazole; voriconazole; glucan synthesis inhibitor; caspofungin; micafungin; anidulafungin; polyenes; amphotericin B; amphotericin B Colloidal Dispersion (ABCD); and griseofulvin.

Exemplary analgesics may include, but are not limited to opiate derivative, codeine, meperidine, methadone, and morphine.

LNP

The invention also embraces LNP made by the process described below wherein the LNP encapsulate an API.

Preferably, more than 70% of API is encapsulated in the LNP. More preferably, more than 80% of API is encapsulated in the LNP, most preferably, more than 90% of API is encapsulated in the LNP.

Optionally, liposomes may be of unilamellar. Alternatively, the liposomes may be of multilamellar, or of inverted hexagonal or cubic morphology, or as lipid discs, hollow liposomes, or solid lipid particles.

The mean particle size of LNP made by the process is from about 10 nm to about 2,000 nm, preferably less than 300 nm, more preferably, the mean particle size may be about 10 to 300 nm or about 20 to about 300 nm. Most preferably, the mean particle size is about 20 to 120 nm or about 30 to about 200 nm, most preferably, between about 30 and about 120 nm, about 10 and 120 nm, about 60 and about 100 nm, or 20 to about 80 nm.

In some embodiments, the LNP solution comprises substantially lipid discs. In other embodiments, the LNP solution comprises substantially liposomes.

In some embodiments, the LNP have a polydispersity index from about 0.005 to about 0.8, e.g., 0.005 to about 0.5, 0.01 to about 0.5, 0.01 to about 0.4, 0.01 to 0.2.

Methods for Making Liposome Solutions

Lipid Solution

The lipid solution may be made from the stock solutions of individual lipids that are mixed together. Lipids are preferably dissolved in an organic solvent to make a lipid solution. The organic solvent used for making the lipid solution may be miscible with water. Preferably the solvent may ethanol, methanol, DMSO, propanol, DMF, THF, acetone, dioxane, ethylene glycol, polyethylene glycol and isopropanol. More preferably, the solvent is polyethylene glycol, isopropanol, and ethanol. Preferably, the solvent includes less than 10% water. In some cases, the lipid solution may be made from a mixture of lipids, thereupon dissolving the mixture in an organic solvent. The concentration of the total lipids in the solution may be in the range from about 1 mg/ml to about 200 mg/ml, e.g., from about 1 mg/ml to about 100 mg/ml. More preferably, the concentration of the total lipids in the solution may be in the range from about 5 mg/ml to about 80 mg/ml or form about 10 mg/ml to 100 mg/ml. In some embodiments, the organic solvent is ethanol at a concentration of about 70% or more (e.g., 75% or more, 80% or more, 85% or more, 90% or more, 95% or more, 100%).

The mixture of lipids will be optimized as required for optimal delivery of the API and is readily optimized by routine experimentation by one of ordinary skill in the art. In Example 2 below, the total lipid concentration of the Lipid Solution is 29 mg/ml; the lipids are dissolved in anhydrous ethanol.

In certain embodiments, a water-insoluble API may be dissolved in the lipid solution. The concentration of the API in the lipid solution will depend on the efficacy of the agent and may easily be determined by one of ordinary skill in the art. The lipid/API ratio will determined by the encapsulation power of the LNP to the API.

Preparing an Aqueous Solution with an API (S1)

A water-soluble API may be dissolved in a first aqueous solution (S1). The pH and salinity of the solution may be optimized to accommodate the requirements for the interaction between the API and the lipids to form liposome. These conditions may be readily determined by one of ordinary skill in the art. As shown below in the examples, S1 in Example 6 comprises 20 mM citrate, 0.5 mg/ml of siRNA, pH 5.0. The acidic pH protonates lipid DLinDMA, and the positively charged lipid interact with the negatively charged siRNA to encapsulate siRNA into liposomes. In Example 1, solutions 1, 2, and 3 are the solution of 250 mM $(NH_4)_2SO_4$, pH 6.5.

Preparing an Aqueous Solution without a API (S2)

As will be readily apparent to those of skill in the art, an aqueous solution that lacks an API, referred to as (S2), may be similar to a solution having the agent. Alternatively, S1 and S2 may be different. As shown in Example 6, S2 is a solution of 20 mM citrate and 100 mM NaCl, pH 5.0, while S1 is a solution of 20 mM citrate, pH 5.0.

Liposome Preparation

Mixing the Solutions

The lipid solution and the aqueous solution(s) preferably enter the manifold from different ports, each with a flow rate of from about 1 ml/min to about 6000 ml/min. Preferably, the flow rates may be from about 5 ml/min to about 1000 ml/min. More preferably, the rates may be from about 20 ml/min to about 600 ml/min. In some embodiments, the flow rates are adjusted based on the size of inlet ports to obtain the desired LNP size, morphology, PDI, and manufacturing scales.

In some embodiments, the lipid solution and/or the aqueous solution is introduced via port size of 0.1-0.5 mm at a flow rate about 1 ml/min to about 2,500 ml/min.

In some embodiments, the flow velocity of the lipid solution and/or the aqueous solution is from about 0.002 m/s to about 10 m/s, e.g., from 0.02 m/s to 8 m/s, from 0.2 m/s to 6 m/s. The flow velocity is adjusted based on the size of inlet ports to obtain the desired LNP size, morphology, PDI, and manufacturing scale.

Loading of the API into LNP

By Solution Mixing

In the mixing chamber the lipids are believed to instantaneously assemble into liposome particles. When the drug API is carried by the lipid solution or by aqueous solution, it may be encapsulated in the liposome by either lipophilic or electrostatic interaction, or both, between the API and the lipids.

By Diffusion

The present invention also provides a method of producing LNP that do not contain an API (so-called "empty" LNP). In such embodiments, the API is absent from both the lipid solution and the aqueous solution that are mixed in the manifold. The API may be loaded into the liposomes by the process of diffusion or another process. For example, doxorubicin may be loaded into the liposome with a pH gradient. See U.S. patent application Ser. No. 10/019,200, PCT Publication No. WO 2001/005373, U.S. Pat. Nos. 5,785,987, 5,380,531, 5,316,771, and 5,192,549, all of which are incorporated herein by reference.

Preferably, the API is mixed with a LNP solution to upload the API into the liposome by diffusion. In one aspect, the API is dissolved in an aqueous solution, and the solution is mixed with the empty LNP. In another aspect, the API may be readily soluble in the solution of empty LNP, and therefore, the API may be directly mixed with the solution of the empty LNP.

The volume ratio of the solution of the API to the empty liposome solution of the API is preferably in the range from about 1:50 to about 1:5. A lower volume of the solution is preferred because it avoids a significant dilution to the final liposome solution.

The drug encapsulation efficiency is preferably greater than 70%. More preferably the efficiency is greater than 80%. Most preferably, the efficiency is greater than 90%.

Liposome Concentration Adjustment

Tangent flow filtration may be used to concentrate the liposome solution.

Buffer Change

Residual organic solvent in the LNP solution may be removed by a buffer change. Preferably, the buffer change is performed by tangent flow filtration. In another embodiment, the buffer change may be performed by dialysis.

Sterile Filtration

The liposome solutions are preferably sterilized by passing a 0.22 micron sterile filter.

US patents, patent applications, PCT publications that describe the use of LNP are: U.S. Pat. No. 8,067,390, PCT Publication No. WO 02/100435A1, PCT Publication No. WO 03/015757A1, PCT Publication No. WO 04/029213A2; U.S. Pat. No. 5,962,016, U.S. Pat. No. 5,891,467, U.S. Pat. No. 5,030,453, and U.S. Pat. No. 6,680,068; and US Patent Application Publication No. 2004/0208921, all of which are incorporated herein by reference.

The following examples are illustrative and not restrictive. Many variations of the technology will become apparent to those of skill in the art upon review of this disclosure. The scope of the technology should, therefore, be determined not with reference to the examples, but instead should be determined with reference to the appended claims along with their full scope of equivalents.

EXAMPLES

Materials

All the manifolds used in the examples were made of PEEK polymer and were purchased from a commercially available source.

Methods

Example 1: Preparation of Liposomes with Doxil Lipid Composition

The lipids were dissolved in anhydrous ethanol. Aqueous Solutions 1, 2, 3 were all 250 mM ammonium sulfate, pH 6.5. The composition of the lipid solution is illustrated in the Table of Example 1. The molar ratio of the lipids is substantially the same as the formulation of Doxil which is a clinically used anti-cancer liposome formulation of doxorubicin. One milliliter each of above 4 solutions was loaded into a 20 ml syringe; each syringe was connected to an inlet port of a 5-port manifold by a tubing. Through the tubing, the solutions in the syringes were pumped into the mixing chamber of the manifold by a syringe pump. The pore size (diameter) of the manifold was 1.0 mm or 1.6 mm. The flow rate of the mixing was 5, 10, or 20, or 30, or 40, or 50 ml/min. The liposome solution exited through the outlet port and was collected in a glass vial.

The particle size and polydispersity index were determined by Malvern Zetasizer Nano ZS in HEPES buffered saline (10 mM HEPES, pH 7.4, 138 mM NaCl). The results are presented in FIG. 4A, FIG. 4B, FIG. 4C and FIG. 4D.

Lipid Composition of Example 1

| Lipid | % (molar) | mg/ml |
|---|---|---|
| Hydrogenated Soy PC | 56.5 | 17.24 |
| Cholesterol | 38.0 | 5.76 |
| mPEG2000-DSPE | 5.3 | 5.76 |

Example 2: Preparation of Doxorubicin Loaded Liposomes

The lipids were dissolved in anhydrous ethanol. Aqueous Solutions 1, 2, 3 were all 250 mM ammonium sulfate, pH 6.5. The composition of the lipid solution are illustrated in the Table of Example 2. The molar ratio of the lipids is substantially the same as the formulation of Doxil which is an anti-cancer liposomal formulation of doxorubicin. One milliliter each of above 4 solutions was loaded into a 20 ml syringe; each syringe was connected to an inlet port of a five-port manifold by a tubing. Through the tubing, the solutions in the syringes were pumped into the mixing chamber of the manifold by a syringe pump. The pore size (diameter) of the mixer was 0.5 mm, and the flow rate was 40 ml/min. The liposome solution exited through the outlet port and was collected in a glass vial. The buffer was changed into histidine/sucrose buffer (12.5 mM histidine, 9.2% sucrose, pH 6.5) by dialysis. The Z-average particle size was 86.1 nm with PDI of 0.021.

Two milliliters of empty liposomes was mixed with 0.198 ml of doxorubicin solution at a concentration of 10 mg/ml in histidine/sucrose buffer. and incubated at 42° C. for 2 hours. The lipid/doxorubicin ratio (w/w) was 7.99, 99.5% of doxorubicin was loaded into the liposome. The Z-average particle size of the loaded liposome was 87.3 nm with PDI of 0.032.

The Cryo-TEM images of doxorubicin-loaded liposomes made by this method was shown in FIG. 5.

Lipid Composition of Example 2

| | % (molar) | mg/ml |
|---|---|---|
| Hydrogenated Soy PC | 56.5 | 17.24 |
| Cholesterol | 38.0 | 5.76 |
| mPEG2000-DSPE | 5.3 | 5.76 |

Example 3: Preparation of Liposomes Using a 6-Port Manifold

The lipids were dissolved in anhydrous ethanol. One milliliter of lipid solution was loaded into a 5-ml syringe, the ammonium sulfate solution (250 mM, pH 6.5) was loaded into four 5-ml syringes with 1 ml for each syringe. Each syringe was connected to an inlet port of a 6-port manifold (IDEX Health & Sciences, part# P-152) by a tubing. The lipids and the ammonium sulfate solutions loaded in the syringes were pumped into the mixing chamber of the manifold by a syringe pump. The pore size of the 6-port manifold was 1.0 mm and the flow rate was 20 ml/min. The liposome solution exited through the outlet port and was collected in a glass vial.

The Z-average particle size and polydispersity index determined by Malvern Zetasizer Nano ZS in HEPES buffered saline (10 mM HEPES, pH 7.4, 138 mM NaCl) were 80.2 nm and 0.207, respectively.

Lipid Composition of Example 3

| | % (molar) | mg/ml |
|---|---|---|
| Hydrogenated Soy PC | 56.5 | 17.24 |
| Cholesterol | 38.0 | 5.76 |
| mPEG2000-DSPE | 5.3 | 5.76 |

Example 4: Preparation of Liposomes Using a 7-Port Manifold

The lipids were dissolved in anhydrous ethanol. One milliliter of lipid solution was loaded into a 5-ml syringe, the ammonium sulfate solution (250 mM, pH 6.5) was loaded into five 5-ml syringes with 1 ml for each syringe. Each syringe was connected to an inlet port of a 7-port manifold (IDEX Health & Sciences, part# P-150) by a tubing. The lipids and the ammonium sulfate solutions loaded in the syringes were pumped into the mixing chamber of the manifold by a syringe pump. The pore size of the 7-port manifold was 1.0 mm and the flow rate was 20 ml/min. The liposome solution exited through the outlet port and was collected in a glass vial The Z-average particle size and polydispersity index determined by Malvern Zetasizer Nano ZS in HEPES buffered saline (10 mM HEPES, pH 7.4, 138 mM NaCl) were 60.1 nm and 0.120, respectively.

Lipid Composition of Example 4

| | % (molar) | mg/ml |
|---|---|---|
| Hydrogenated Soy PC | 56.5 | 17.24 |
| Cholesterol | 38.0 | 5.76 |
| mPEG2000-DSPE | 5.3 | 5.76 |

Example 5: Preparation of Liposomes Using a 9-Port Manifold

The lipids were dissolved in anhydrous ethanol. One milliliter of lipid solution was loaded into a 5-ml syringe, the ammonium sulfate solution (250 mM, pH 6.5) was loaded into seven 5-ml syringes with 1 ml for each syringe. Each syringe was connected to an inlet port of a 9-port manifold (IDEX Health & Sciences, part# P-191) by a tubing. The lipids and the ammonium sulfate solutions loaded in the syringes were pumped into the mixing chamber of the manifold by a syringe pump. The pore size of the 9-port manifold was 1.0 mm, and the flow rate was 20 ml/min. The liposome solution exited through the outlet port and was collected in a glass vial The Z-average particle size and polydispersity index determined by Malvern Zetasizer Nano ZS in HEPES buffered saline (10 mM HEPES, pH 7.4, 138 mM NaCl) were 63.1 nm and 0.133, respectively.

Lipid Composition of Example 5

|  | % (molar) | mg/ml |
|---|---|---|
| Hydrogenated Soy PC | 56.5 | 17.24 |
| Cholesterol | 38.0 | 5.76 |
| mPEG2000-DSPE | 5.3 | 5.76 |

Example 6: Preparation of siRNA Liposomes

Lipid solution: The components of the lipids solution was illustrated in the Table of Example 6.

The RNA was siApoB-1 sequence as described in 61/791,054 in Example 6.

Aqueous Solution 1: siRNA: 0.5 mg/ml in a citrate buffer (20 mM, pH 5.0); Aqueous Solution 2: 20 mM citrate, pH 5.0, 100 mM NaCl; Aqueous Solution 3: same as Solution 2

One milliliter of each of above 4 solutions was loaded into a 20 ml syringe; each syringe was connected to an inlet port of a 5-port manifold by a tubing. The lipids, siRNA, and the aqueous buffer solutions loaded in the syringes were pumped into the mixing chamber of the manifold by a syringe pump. The liposome solution exited through the outlet port and was collected in a glass vial The pore size of the 5-port manifold mixer was 1 mm or 1.6 mm. The flow rate was 5, or 10, or 30, or 40, or 50 ml/min.

The particle size and PDI of siRNA liposomes were determined by Malvern Zetasizer Nano ZS in HEPES buffered saline (10 mM HEPES, pH 7.4, 138 mM NaCl), The particle morphology was imaged by Cryo-TEM. The results are shown in FIG. 6. As shown in the figure, lipids form unilamellar liposomes, in which doxorubicin forms crystals.

Lipid Solution in Anhydrous Ethanol of Example 6

|  | % (molar) | mg/ml |
|---|---|---|
| 1,2-dilinoleyloxy-3-dimethylaminopropane (DLinDMA) | 38.7 | 2.775 |
| Cholesterol | 46.4 | 2.095 |
| DSPC | 13.0 | 1.200 |
| mPEG2000-DMA | 1.9 | 0.570 |

Example 7: Preparation of Liposome and Lipid Discs from the Same Formulation by Altering the Flow Rate The lipids were dissolved in anhydrous ethanol. Aqueous Solutions 1, 2, 3 were all 250 mM ammonium sulfate, pH 6.5. The composition of the lipid solution are illustrated in the Table of Example 7. One milliliter each of the above 4 solutions was loaded into a 20 ml syringe; each syringe was connected to an inlet port of a five-port manifold by tubing. Through the tubing, the solutions in the syringes were pumped into the mixing chamber of the manifold by a syringe pump. The pore size (diameter) of the manifold was 1.0 mm, and the flow rate was 40 ml/min, or 5 ml/min. The liposome or lipid disc solution exited through the outlet port and was collected in a glass vial. The buffer was changed into HEPES buffer (10 mM HEPES, 138 mM NaCl, pH 7.5) by dialysis. The liposome was loaded with doxorubicin. The Cryo-TEM imaging identified that the 40 ml/min flow rate generated unilamellar liposomes (FIG. 7A) having a Z-average particle size of 86.1 nm and a PDI of 0.021. The 5.0 ml/min flow rate predominantly generated lipids discs (FIG. 7B) with about 60 nm in diameter and about 6 nm lipid bilayer thickness.

Lipid Composition of Example 7

|  | % (Molar) | mg/ml |
|---|---|---|
| Hydrogenated Soy PC | 56.6 | 21.9 |
| Cholesterol | 38.4 | 7.3 |
| mPEG2000-DSPE | 5.0 | 7.3 |

Example 8: The Effects of Number and Position of the Exit Ports on Liposome Particle Size The lipids were dissolved in anhydrous ethanol. Aqueous Solutions 1, 2, 3 were all 250 mM ammonium sulfate, pH 6.5. The composition of the lipid solution is illustrated in the Table of Example 7. One milliliter each of above 4 solutions was loaded into a 20 ml syringe; each syringe was connected to an inlet port of a seven-port manifold by tubing (configured variously as shown in FIGS. 8A-8D). Through the tubing, the solutions in the syringes were pumped into the mixing chamber of the manifold by a syringe pump. The pore size (diameter) of the manifold was 0.5 mm, and the flow rate was 35 ml/min. One (1) or two (2) or three (3) of the rest 3 ports (the center one perpendicular to other ports and two side ports, see the illustration in FIG. 8) was (were) used as the outlet port(s) for the liposome solution. The liposome solution exited through the outlet port(s) and was collected in a glass vial. The different number of outlet ports resulted in different liposome particle sizes: 91 nm (PDI 0.146) for 3 ports of outlet (FIG. 8A), 81 nm (PDI 0.089) for two ports outlet (FIG. 8B); and 74-75 nm (PDI 0.052-0.088) for one port outlet (FIGS. 8C and 8D). The position of the outlet had no significant effects on the particle size (FIGS. 8C and 8D). Therefore, the liposome particle size can be controlled via the numbers of the outlet ports.

Lipids Composition of Example 8

|  | % (Molar) | mg/ml |
|---|---|---|
| Hydrogenated Soy PC | 56.6 | 30.8 |
| Cholesterol | 38.4 | 10.3 |
| mPEG2000-DSPE | 5.0 | 10.3 |

The invention claimed is:
1. A method for preparing lipid nanoparticles (LNP), the method comprising:
  a) introducing i) one or more streams of a lipid solution via a first set of one or more inlet ports of a manifold and ii) one or more streams of an aqueous solution via a second set of one or more an inlet ports of the manifold, thereby mixing the lipid solution and the aqueous solution so as to produce an LNP solution; and b) recovering the LNP solution via one or more outlet ports of the manifold;

wherein the angle between at least one lipid and at one aqueous solution inlet ports is not 180° or a substantially similar angle, wherein the flow velocity of the LNP solution is at least about 0.2 m/s and the flow rate is at least 50 ml/minute, and wherein the lipid solution comprises lipids dissolved in an organic solvent.

2. The method of claim 1, wherein the angle between at least one lipid and at one aqueous solution inlet ports is about 120° or less.

3. The method of claim 1, wherein the aqueous solution in step ii) is introduced via at least two inlet ports.

4. The method of claim 3, wherein the aqueous solution in step ii) is introduced via at least 3 but no more than 11 inlet ports.

5. The method of claim 3, wherein at least two aqueous inlet ports and at least one lipid solution inlet port are in the same plane.

6. The method of claim 5, wherein at least one outlet port is substantially perpendicular to the plane of inlet ports.

7. The method of claim 5, wherein at least one outlet port is substantially not perpendicular to the plane of inlet ports.

8. The method of claim 3, wherein at least two aqueous solution inlet ports and at least on lipid solution inlet port are not in the same plane.

9. The method of claim 1, wherein the lipid solution and/or the aqueous solution is introduced at a flow rate of up to 6,000 ml/min.

10. The method of claim 9, wherein the lipid solution and/or the aqueous solution is introduced via port size of 0.1-5 mm.

11. The method of claim 1, wherein the flow velocity of the lipid solution and/or the aqueous solution is from about 0.2 m/s to about 6 m/s.

12. The method of claim 1, wherein the LNP solution comprises substantially lipid discs.

13. The method of claim 1, wherein the LNP solution comprises substantially liposomes.

14. The method of claim 1, wherein the mean particle size of LNP is from about 10 nm to about 2,000 nm.

15. The method of claim 1, wherein the LNP have a polydispersity index from about 0.0005 to about 0.5.

16. The method of claim 1, wherein the organic solvent is ethanol at a concentration of about 70% or more.

17. The method of claim 1, wherein the concentration of total lipids in the lipid solution is in the range from about 1 mg/ml to about 200 mg/ml.

18. The method of claim 1, wherein one of the lipids in the lipid solution is chosen from anionic lipid, cationic lipid, or neutral lipid.

19. The method of claim 3, wherein the aqueous solution introduced into at least one of the inlet ports differs from a second aqueous solution introduced into another inlet port.

20. The method of claim 1, wherein the aqueous solution and/or the lipid solution comprises an active pharmaceutical ingredient (API).

21. The method of claim 1, wherein step a) further comprises introducing iii) two or more streams of non-aqueous solutions via two or more inlet ports of the manifold.

22. The method of claim 1, further comprising step c) loading LNP recovered from the LNP solution with an API.

23. The method of claim 20 or claim 22, wherein the API is a small molecule, a peptide, a protein, RNA, or DNA.

24. The method of claim 20 or claim 22, wherein the API is an anticancer agent, an antibiotic agent, an antiviral agent, an anti-fungal agent, or an analgesic.

25. The method of claim 24, wherein the anti-cancer agent is chosen from daunorubicin, doxorubicin, paclitaxel, docetaxel, cisplatin, carboplatin, cytarabine, floxuridine, fludarabine, fluorouracil, iproplatin, leuprolide acetate, and methotrexate.

* * * * *